(12) United States Patent
Wang et al.

(10) Patent No.: US 7,496,172 B2
(45) Date of Patent: Feb. 24, 2009

(54) METHOD FOR EXAMINING DEFECT IN STEEL BAR AND APPARATUS THEREFOR

(75) Inventors: Chung-Yue Wang, Jhongli (TW); Peng-Ching Peng, Jhongli (TW)

(73) Assignee: National Central University, Jhongli (TW)

( * ) Notice: Subject to any disclaimer, the term of this patent is extended or adjusted under 35 U.S.C. 154(b) by 50 days.

(21) Appl. No.: 11/583,126

(22) Filed: Oct. 19, 2006

(65) Prior Publication Data

US 2008/0084556 A1   Apr. 10, 2008

(30) Foreign Application Priority Data

Oct. 5, 2006   (TW) .............................. 95137157 A

(51) Int. Cl.
G01B 15/06 (2006.01)
G01N 23/02 (2006.01)
(52) U.S. Cl. ............................ 378/58; 378/56; 378/207
(58) Field of Classification Search .................. 378/56, 378/58, 207
See application file for complete search history.

(56) References Cited

U.S. PATENT DOCUMENTS 5,210,783 A * 5/1993 Wallace ...................... 378/207
H1495 H * 10/1995 Kirchner et al. ............... 378/22
5,828,723 A * 10/1998 Mariscotti ..................... 378/58
5,864,601 A * 1/1999 Cattorini et al. ............... 378/59
6,333,962 B1 * 12/2001 Kitaguchi et al. ............. 378/57
6,658,089 B1 * 12/2003 Mohr et al. .................. 378/162
2006/0126784 A1 * 6/2006 Wang .......................... 378/51

FOREIGN PATENT DOCUMENTS

JP   59148853 A * 8/1984
JP   60236051 A * 11/1985

\* cited by examiner

*Primary Examiner*—Edward J Glick
*Assistant Examiner*—Thomas R Artman
(74) *Attorney, Agent, or Firm*—Troxell Law Office, PLLC

(57) ABSTRACT

A penetrating radiation is used to examine a steel bar in a reinforced concrete coordinated with a comparing object. The position and size of the comparing object are known in advance. At first, the steel bar and the comparing object are projected on an imaging device. Then, a magnifying rate of an image size of the comparing object shown on the imaging device is calculated. By using the magnifying rate and by comparing the image sizes of the steel bar and the comparing object on the imaging device, the defect size of the steel bar can be figured out.

7 Claims, 2 Drawing Sheets

METHOD FOR EXAMINING DEFECT IN STEEL BAR AND APPARATUS THEREFOR

FIELD OF THE INVENTION

Figure 1:
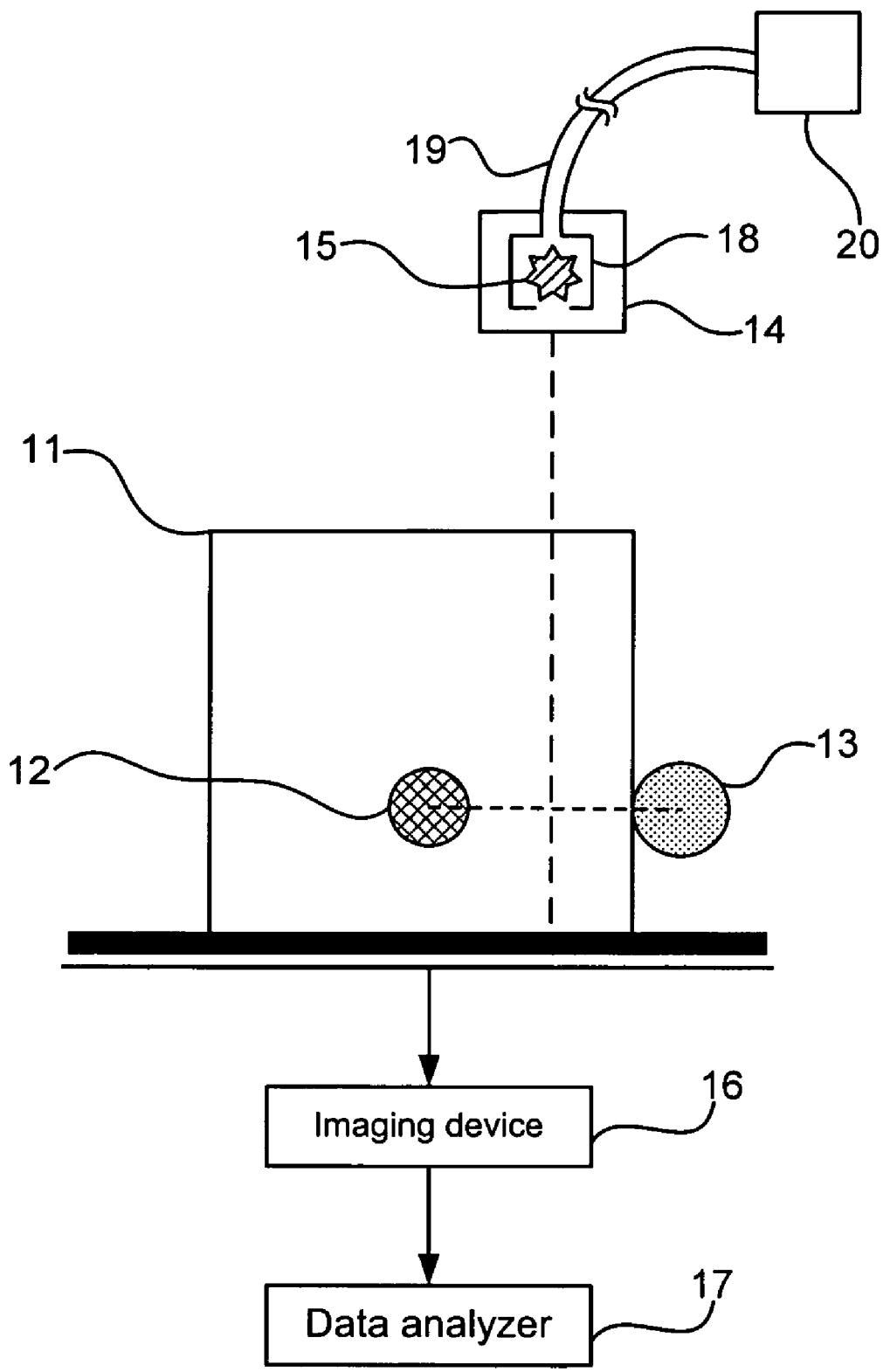

The present invention relates to examining a steel bar; more particularly, relates to using a penetrating radiation for examining the steel bar in a reinforced concrete, and using a magnifying rate of image of a comparing object projected on an imaging device for figuring out defect size of the steel bar.

DESCRIPTION OF THE RELATED ARTS

Defect of a steel bar in a reinforced concrete is generally examined with electromagnetism. But, this method is greatly affected by magnetic conductivity, electric conductivity, distance between steel bars and joint of steel bars, which increase difficulties in examining steel bars.

For example, a steel bar detector using eddy current is developed. A detector having an alternating wire coil is located near detected steel bar protecting layer to produce a number of eddy-like currents at an alternating magnetic field of the steel bar through electromagnetic indication. And, by the changes in signal of eddy currents, a position and a size of the steel bar are detected. Yet, in places having multiple steel bars or jointing steel bar, interferences to electromagnetic induction occur with the neighboring steel bars and so detection using electromagnetic induction would fail in such an situation. Hence, the prior arts do not fulfill users' requests on actual use.

SUMMARY OF THE INVENTION

The main purpose of the present invention is to use a penetrating radiation for examining the steel bar, and use a magnifying rate of an image size of a comparing object for calculating out a defect size of the steel bar.

To achieve the above purpose, the present invention is a method for examining a defect in a steel bar and an apparatus therefor. The method comprises steps of: (a) obtaining a reinforced concrete; (b) detecting a position of a steel bar in the reinforced concrete; (c) locating a spherical comparing object outside of the reinforced concrete to correspond to the steel bar; (d) locating a radiation source outside of the reinforced concrete on a center line between the steel bar and the comparing object for radiating a penetrating radiation; (e) projecting the steel bar and the comparing object on an imaging device with the radiation to measure image sizes of the steel bar and the comparing object; and (f) using the magnifying rate of the image size of the comparing object to figure out a defect size of the steel bar.

And, the apparatus for the method comprises a reinforced concrete with a steel bar; a spherical comparing object being located outside of the reinforced concrete and corresponding to the steel bar; a radioactive examining device comprising a radiation source, a radiation shield, a radiation controller and a radiation channel; an imaging device; and a data analyzer, where the radiation source is located on a center line between the steel bar and the comparing object; the radiation source radiates a high-energy ray penetrating through the steel bar and projects the steel bar and the comparing object on the imaging device; and the data analyzer analyzes the images to figure out defect size of the steel bar. Accordingly, a novel method for examining a defect in a steel bar and an apparatus therefor are obtained.

BRIEF DESCRIPTIONS OF THE DRAWINGS

Figure 2:
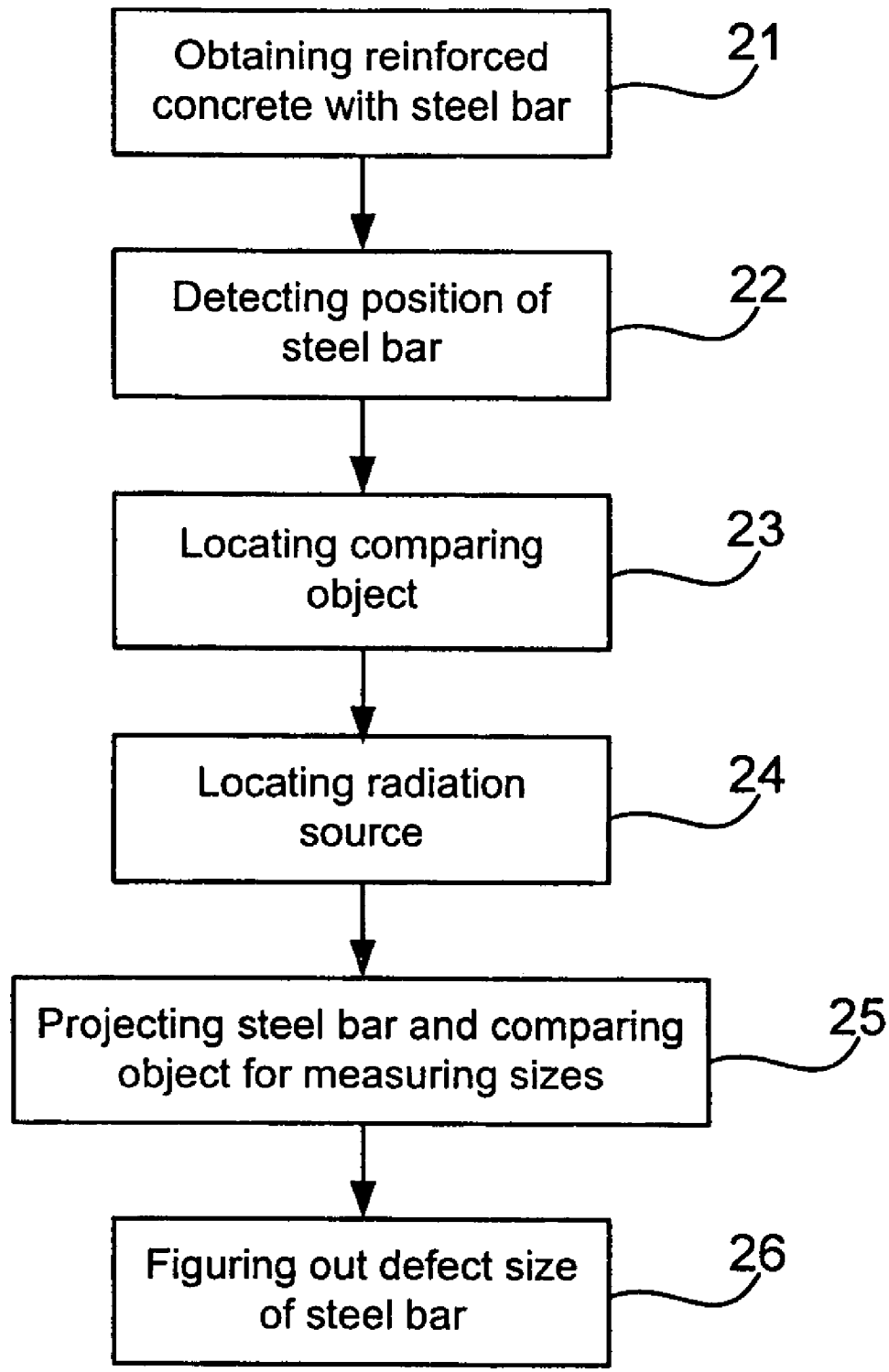

The present invention will be better understood from the following detailed description of the preferred embodiment according to the present invention, taken in conjunction with the accompanying drawings, in which FIG. 1 is the view showing the apparatus of the preferred embodiment according to the present invention; and FIG. 2 is the flow view showing the method of the preferred embodiment.

DESCRIPTION OF THE PREFERRED EMBODIMENT

The following description of the preferred embodiment is provided to understand the features and the structures of the present invention.

Please refer to FIG. 1, which is a view showing an apparatus of a preferred embodiment according to the present invention. As shown in the figure, the present invention is a method for examining a defect in a steel bar and an apparatus therefor. The apparatus comprises a reinforced concrete 11 having a steel bar 12; a spherical comparing object 13 being located outside of the reinforced concrete 11 and corresponding to the steel bar 12; a radioactive examining device 14 comprising a radiation source 15, a radiation shield 18, a radiation controller 19 and a radiation channel 20; an imaging device 16; and a data analyzer 17, where the radiation source 15 is located on a center line between the steel bar 12 and the comparing object 13 to radiate a ray penetrating through the reinforced concrete 11 to project the steel bar 12 and the comparing object 13 on the imaging device 16; and the data analyzer 17 is used to analyze the images projected to figure out defect size of the steel bar.

Please refer to FIG. 2, which is a flow view showing a method of the preferred embodiment. As shown in the figure, a method of the preferred embodiment comprises the following steps:

(a) Obtaining reinforced concrete with steel bar 21: A reinforced concrete having a steel bar is obtained.

(b) Detecting position of steel bar 22: The position of the steel bar in the reinforced concrete is detected.

(c) Locating comparing object 23: A comparing object is located outside of the reinforced concrete and is a spherical object corresponding to the steel bar.

(d) Locating radiation source 24: A radiation source is located outside of the reinforced concrete on a center line between the steel bar (or inner defect) and the comparing object; the radiation source radiates a penetrating ray of Ir-192, Co-60 or Cs-137; and the radiation intensity of the ray is 75 Ci (Curie).

(e) Projecting steel bar and comparing object for measuring sizes 25: The ray is radiated through the reinforced concrete from the radiation source for projecting the steel bar and the comparing object on the imaging device; and image sizes of the steel bar and the comparing object are measured.

(f) Calculating defect size of steel bar 26: A magnifying rate of the image size of the comparing object on the imaging device is figured out; and the magnifying rate is used to calculate defect size of the steel bar.

Thus, a novel method for examining a defect in a steel bar and an apparatus therefor are obtained. In the present invention, a penetration characteristic of a radioactive ray is used for an examination. The radioactive ray has a high energy and an even radiation intensity; the radiation source has a small size; no extra energy is required for radiating the ray; and the radiation source can be easily placed at any complex structure. Hence, the radiation source can be located at places for a complete examination; and so the safety of a structure can be evaluated by calculating defect size of the steel bar.

To sum up, the present invention is a method for examining a defect in a steel bar and an apparatus therefor, where a penetrating radiation of low cost and easy operation is used for examination and a magnifying rate of image size of a comparing object projected on an imaging device is used for figuring out defect size of a steel bar.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method for examining a defect in a steel bar, comprising steps of:
    (a) obtaining a reinforced concrete having a steel bar;
    (b) obtaining position of said steel bar;
    (c) locating a comparing object outside of said reinforced concrete;
    (d) locating a radiation source outside of said reinforced concrete;
    (e) radiating a ray penetrating through said reinforced concrete to project said reinforced concrete and said comparing object on an imaging device; and
    (f) obtaining defect size of said steel bar with images of said reinforced concrete and said comparing object obtained from said radiating step,
    wherein said radiation source radiates a ray selected from a group consisting of Ir(Iridium)-192, Co(Cobalt)-60 and Cs(Cesium)-137; and
    wherein said ray has a radiation intensity between 68Ci (Curie) and 82Ci
    wherein said comparing object is a spherical object.

2. The method according to claim 1, wherein said comparing object is located at a position corresponding to said steel bar.

3. The method according to claim 1, wherein said radiation source is further located on a center line between said steel bar and said comparing object.

4. The method according to claim 1, wherein said method has an apparatus comprising:
    a reinforced concrete, said reinforced concrete having a steel bar;
    a comparing object, located at a position corresponding to said steel bar;
    a radioactive examining device, said radioactive examining device having a radiation source, said radiation source being located on a center line between said steel bar and said comparing object;
    an imaging device, said imaging device displaying images of said reinforced concrete and said comparing object; and
    a data analyzer, said data analyzer analyzing said images and figuring out defect size of said steel bar.

5. The method according to claim 4, wherein said radioactive examining device further comprises a radiation shield, a radiation controller and a radiation channel.

6. A method for examining a defect in a steel bar, comprising steps of:
    (a) obtaining a reinforced concrete having a steel bar;
    (b) obtaining position of said steel bar;
    (c) locating a comparing object outside of said reinforced concrete;
    (d) locating a radiation source outside of said reinforced concrete;
    (e) radiating a ray penetrating through said reinforced concrete to project said reinforced concrete and said comparing object on an imaging device; and
    (f) obtaining defect size of said steel bar with images of said reinforced concrete and said comparing object obtained from said radiating step,
    wherein said radiation source radiates a ray selected from a group consisting of Ir(Iridium)-192, Co(Cobalt)-60 and Cs(Cesium)-137; and
    wherein said ray has a radiation intensity between 68Ci (Curie) and 82Ci,
    wherein said radiation source is further located on a center line between said steel bar and said comparing object.

7. A method for examining a defect in a steel bar, comprising steps of:
    (a) obtaining a reinforced concrete having a steel bar;
    (b) obtaining position of said steel bar;
    (c) locating a comparing object outside of said reinforced concrete;
    (d) locating a radiation source outside of said reinforced concrete;
    (e) radiating a ray penetrating through said reinforced concrete to project said reinforced concrete and said comparing object on an imaging device; and
    (f) obtaining defect size of said steel bar with images of said reinforced concrete and said comparing object obtained from said radiating step,
    wherein said radiation source radiates a ray selected from a group consisting of Ir(Iridium)-192, Co(Cobalt)-60 and Cs(Cesium)-137; and
    wherein said ray has a radiation intensity between 68Ci (Curie) and 82Ci,
    wherein said method has an apparatus comprising:
    a reinforced concrete, said reinforced concrete having a steel bar;
    a comparing object, said comparing object being a spherical object, said comparing object located at a position corresponding to said steel bar;
    a radioactive examining device, said radioactive examining device having a radiation source, said radiation source being located on a center line between said steel bar and said comparing object;
    an imaging device, said imaging device displaying images of said reinforced concrete and said comparing object; and
    a data analyzer, said data analyzer analyzing said images and figuring out defect size of said steel bar.

* * * * *